United States Patent
Mathisen et al.

(10) Patent No.: US 8,697,172 B2
(45) Date of Patent: Apr. 15, 2014

(54) DRINK FORMULA COMPRISING FRESH MARINE OMEGA-3 OIL AND ANTIOXIDANTS

(75) Inventors: Janne Sande Mathisen, Oslo (NO); Henrik Mathisen, Oslo (NO)

(73) Assignee: Smartfish AS, Oslo (NO)

( * ) Notice: Subject to any disclaimer, the term of this patent is extended or adjusted under 35 U.S.C. 154(b) by 335 days.

(21) Appl. No.: 12/934,344

(22) PCT Filed: Mar. 26, 2009

(86) PCT No.: PCT/NO2009/000112
§ 371 (c)(1),
(2), (4) Date: Feb. 17, 2011

(87) PCT Pub. No.: WO2009/120091
PCT Pub. Date: Oct. 1, 2009

(65) Prior Publication Data
US 2011/0135745 A1    Jun. 9, 2011

(30) Foreign Application Priority Data
Mar. 27, 2008 (NO) .................................. 20081487

(51) Int. Cl.
*A23D 7/005* (2006.01)
*A23L 1/303* (2006.01)
*A61K 31/202* (2006.01)
*A61K 31/07* (2006.01)

(52) U.S. Cl.
USPC .............. 426/601; 426/73; 514/943; 514/725

(58) Field of Classification Search
USPC ............................ 426/601, 73; 514/943, 725
See application file for complete search history.

(56) References Cited

U.S. PATENT DOCUMENTS

| | | | |
|---|---|---|---|
| 4,963,380 A | 10/1990 | Schroder et al. | 426/330.3 |
| 2004/0015000 A1* | 1/2004 | Aanesen et al. | 554/8 |
| 2006/0105033 A1 | 5/2006 | Bendich | 424/451 |
| 2006/0228403 A1 | 10/2006 | Zimmerman | 424/450 |
| 2008/0058418 A1 | 3/2008 | D'Angelo et al. | 514/560 |

FOREIGN PATENT DOCUMENTS

| | | |
|---|---|---|
| WO | 9117670 | 11/1991 |
| WO | 0067745 | 11/2000 |
| WO | 01/47377 | 7/2001 |
| WO | 03/105606 | 12/2003 |
| WO | 2004/075647 | 9/2004 |
| WO | 2004/112776 | 12/2004 |
| WO | 2007/001185 | 1/2007 |
| WO | 2007/064222 | 6/2007 |
| WO | 2007114945 | 10/2007 |
| WO | 2007/149590 | 12/2007 |
| WO | 2009/002184 | 12/2008 |

OTHER PUBLICATIONS

Voluntary Monograph, Counsel for Responsible Nutrition, 6 pp., 2006.*

(Continued)

*Primary Examiner* — Rosanne Kosson
(74) *Attorney, Agent, or Firm* — Fitzpatrick, Cella, Harper & Scinto

(57) ABSTRACT

The present invention relates a new drink formula comprising fresh marine omega-3 oil in an emulsion and antioxidants well known to be health promoting to humans, and process for the production of said drink and the use of said drink for production of a medicament.

12 Claims, 1 Drawing Sheet

Degree of lipid peroxidation in U937 cells

(56) References Cited

OTHER PUBLICATIONS

Norwegian Search Report issued Sep. 29, 2008 in Norwegian Application No. 20081487.

"The omega-3 Series Smartfish." Datasheet (online). Marine Harvest, Feb. 27, 2008. Retrieved on Sep. 22, 2010. <Url:http://www.marineharvest.com/en/products1/product-highlights/the-omega-3-series-smartfish/#>.

* cited by examiner

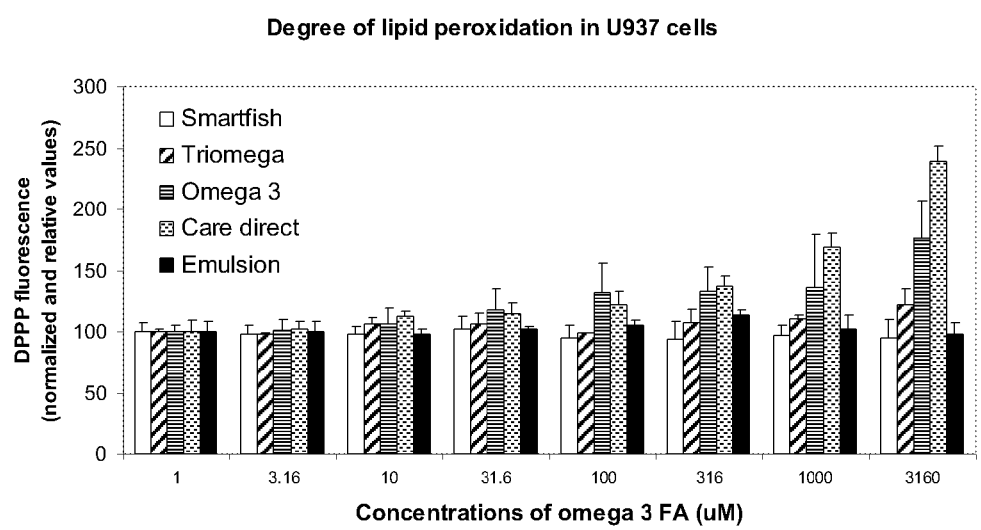

DRINK FORMULA COMPRISING FRESH MARINE OMEGA-3 OIL AND ANTIOXIDANTS

FIELD OF INVENTION

The present invention relates a new drink formula comprising fresh marine omega-3 oil in an emulsion and antioxidants well known to be health promoting to humans, a process for the production of said drink and the use of said drink for production of a medicament.

DESCRIPTION OF PRIOR ART

The health promoting effects of polyunsaturated oils are well known. The health promoting effects of antioxidants are also known. However, it is a need for a composition combining these nutrients in a formula that result in increased absorption and where the body is able to utilize the nutrients optimally.

There is a need for new compositions where these native unstable health promoting nutrients are formulated such as each component is keep intact and fresh.

The effects of omega-3 fatty acids (EPA, DHA and DPA) on a number of diseases and conditions, such as cardiovascular, mental, skin and ageing, are well documented. Supplementation of omega-3 increases world wide. There is an increase in the consumption of omega-3 containing products, and omega-3 in the form of fish and/or food supplement is highly recommended by health authorities.

Oxidative stress is a sort of "chemical stress" induced by the presence in our body of abnormal quantities of free radicals. Whatever the cause, oxidative stress is believed to be responsible of early ageing and of a very long series of common diseases—about one hundred—that span from arterial hypertension to atherosclerosis, from infarct to ictus, from Parkinson's to Alzheimer's, from colitis to pancreatitis, from obesity to diabetes, from chronic bronchitis to rheumatoid arthritis, from AIDS to several types of cancer.

The body is protected against free radicals by antioxidants, both self-produced and antioxidants supplied through food and drinks. Antioxidants may be vitamins, minerals, and enzymes, either fat soluble or water soluble.

In situations where the body is subjected to enhanced oxidation (a lot of free radicals), the body might not have sufficient antioxidants to neutralize or quench the free radicals. Destructive chain reactions occur, which might cause increased and detrimental oxidative stress.

A conventional method for measuring the oxidative status is FRAS (Free Radical Analytical System.) The test is evaluated in a conventional measuring unit called U.Carr (from the chemist Carratelli, the inventor of the test). The method is quick and only a drop of blood drawn from the finger tip is required.

The below table gives an overview of normal and elevated oxidative values.

| FRAS values: | |
| --- | --- |
| Normal values | 250-300 U.Carr |
| Boarderline values | 300-320 U.Carr (showing a slightly elevated level of free radicals which could lead to oxidative stress conditions) |
| Mild oxidative stress | 320-340 U.Carr |
| Moderate oxidative stress | 340-400 U.Carr |
| Severe oxidative stress | 400-500 U.Carr |

The theoretical basis for the effects of antioxidants is well acknowledged. It is also acknowledged that the absorption of antioxidants in the body from antioxidant supplements is a challenge. However, studies have demonstrated that antioxidants in a non-native form or as isolated vitamins are inadequately taken up by the body. Some studies indicate that ingestion of high dosages of isolated vitamins may convert antioxidants to prooxidants, thus leading to elevated oxidation in the body. Studies and literature indicates better absorption and bioavailability of antioxidants naturally present when consumed in foods e.g. as fruits and vegetables.

It is known that humans having severe oxidative stress are often deficient in omega-3 fatty acids (DHA and EPA), and possess a low antioxidative status.

Oxidative damage and antioxidant deficiency is now regarded as crucial factors to many diseases, and are probably the primary reason for an imperfect replacement of old damaged cells by new cells.

Research work has demonstrated that oxidation products of fatty acids are highly reactive and may affect and interfere with intracellular processes. Many commercially available omega-3 supplements contain fish oil having a significant degree of oxidation, which in turn may induces adverse effects on intracellular processes.

Although these dietary supplements often are added antioxidants, this will not reverse the rancidity already present in the dietary supplement. On the other hand, to prevent further oxidation of the unsaturated fish oil, the antioxidants in the supplement will be consumed and finally (after some months) cease. Thus, antioxidants in the commercially available dietary supplements will not induce any health promoting effects in humans.

Thus, there is a need for a new composition combining fresh fish oil and specific antioxidants to provide a new drink formula having improved health promoting effects on humans.

SUMMARY OF THE INVENTION

Thus, the object of the present invention is to provide a new drink formula comprising fresh marine omega-3 oil and antioxidants well known to be health promoting to humans.

A further object of the present invention is to provide a process for the production of the new drink formula, wherein the fish oil is emulsified and handled under gentle conditions through a minimum of process steps.

A further object of the present invention is to provide a drink for use as a therapeutic drink. The specific antioxidants to be included in the drink are selected according to the disease or disorder to be treated.

These and further objects are achieved by the present invention.

DETAILED DESCRIPTION OF THE INVENTION

Hence, the present invention relates to a drink combining fresh marine oil and specific antioxidants. The antioxidants having a health promoting effect on humans are present in the drink to reduce oxidative stress of the human being, not for the purpose of oil stabilization in the preparation. The drink may be a functional drink or a therapeutic drink, a thirst-quencher or an ordinary drink. Preferably, the drink has a base containing natural antioxidants eg. fruit or vegetable juice, green tea, but any drinkable liquid may be used.

The new drink combines the stable omega-3 emulsion known from prior art, and well known health promoting antioxidants. The drink reveals surprising characteristics as to absorption of antioxidants and the effect of antioxidants on the body. Compared to prior art where corresponding amounts of omega-3 and antioxidants are ingested in different formulas, the drink according to the present invention shows improved delivery, improved uptake and improved effect on oxidative stress.

Both the omega-3 oil and the antioxidants contained in the drink according to the invention are remarkable stable in the composition, and the progress of rancidity and loss of antioxidant effects are much lower than in known product formulated as separate capsules.

One aspect of the present invention relates to a drink comprising fresh marine oil in an oil-in-water emulsion wherein the marine oil has a totox value below 10, further added at least one antioxidant not naturally present in said oil-in-water emulsion.

The term fresh marine oil describes an oil prepared from fresh fish where all process steps are conducted carefully and under strict oxygen control according to functional oil standards in order to prevent oil oxidation. The fresh marine oil will have a low oxidative status, revealing a colourless oil without the characteristic smell or taste of fish. The level of oxidation given as the totox value (2 times the peroxide value (PV) added with the anisidin value (AV)) should be below 10, preferably below 8, and most preferably below 5. Marine oil present in many food supplements today contains oil with a much higher totox value, typically 20-30 or even higher.

The fresh marine oil may be any oil rich in omega-3, e.g. fish oil, seal oil or krill oil. The oil may be mixed with other polyunsaturated oils of vegetable origin such as algae oil and herbal oil such as evening primrose oil and rapeseed oil.

One preferred embodiment of the present invention provides a drink wherein the content of marine oil is about 0.5%-5% by weight based on the total weight, more preferably in the range of 0.5%-3%, most preferably in the range of 1.5%-2.5%.

The oil-in water emulsion is prepared by any conventional method, preferably as described in the applicants own Norwegian applications NO 20044542, 20053136 and 20055620. In said emulsions the antioxidants are present to stabilize the oil during production and storage, not for the purpose of inducing any health promoting effects on humans.

The water phase of the oil-in water emulsion is preferably a water phase containing natural antioxidants e.g. fruit/vegetable juices, green tea, white tea and herbal tea. The juice may be a fresh pressed juice or juice in the form of juice concentrate or juice purrè diluted to obtain a normal ready-to-use juice. The water phase may also contain proteins such as soy, oat proteins, whey proteins and/or milk proteins.

According to the invention, the term added or further added antioxidants are to be understood as antioxidants not naturally present in the water or oil phase, but added separately. The further added antioxidant may be similar to one or more antioxidants naturally present in the water or oil phase, or different. The further added at least one antioxidant may be one or a combination of two or more antioxidants.

Antioxidants useful according to the present invention are antioxidants known to have health promoting effects on humans. Useful antioxidants are e.g. astaxanthin, vitamin E, vitamin C, beta-carotene, lutein, lycopene, zeaxanthine, glutathione, flavonoids, carotenoids, plant phenols, polyphenols, coenzyme Q10, resveratrol, curcumin, phycnogenol, selen, copper, zink and magnesium. The antioxidants may be present individually or in a mixture of two or more. The antioxidants may be selected to meet specific purposes, i.e. the desirable health effects to be achieved. As examples, a beverage according to the invention comprising lutein and zeaxanthine will likely have a positive impact on different eye conditions. A beverage according to the invention comprising the antioxidant rich curcumin is suitable to alleviate inflammation and fight infections. A beverage according to the invention comprising CoQ10 may be useful for neurological disorders. Further, a beverage according to the invention comprising pycnogenol may be beneficial for reducing osteoarthritis. Beta-carotene added to the said beverage may be useful for respiratory disorders and CoQ10 and selenium will be useful for cardiovascular disorders.

In one embodiment of the present invention, the drink may be added prebiotics and/or probiotics.

In one embodiment of the present invention, the drink may be carbonated.

A further aspect of the present invention relates to a process for the production of a drink according to the invention comprising the following steps:

a) oil soluble antioxidants and flavouring agents, together with emulsifier are added to the oil phase,
b) water soluble additives are added to the water phase,
c) the oil and water phase are mixed to a homogenous emulsion,
d) the emulsion obtained is optionally subjected to pasteurization and/or homogenization processes,
e) the obtained emulsion is cooled down and filled on clean disposable containers;
wherein all steps are performed under strict oxygen control.

Alternatively, the process for the production of a drink according to the invention comprises the following steps:

a) oil soluble antioxidants and flavouring agents are added to the oil phase,
b) water soluble additives are added to the water phase,
c) the oil and water phase are mixed and the emulsifier is added, followed by gentle mixing to achieve a homogenous emulsion,
d) the emulsion obtained is optionally subjected to pasteurization and/or homogenization processes,
e) the obtained emulsion is cooled down and filled on clean disposable containers;
wherein all steps are performed under strict oxygen control.

A further aspect of the present invention relates a drink for use as a therapeutic drink. Further aspects relate to the use of a drink according to the invention for the production of a medical preparation for the prophylaxis or treatment of diseases associated with elevated oxidative stress, such as cancer, inflammatory disorders, neurological disorders, cardiovascular disorders and respiratory disorders.

It has surprisingly been found that the new drink formula combining fresh omega-3 fatty acids and at least one added antioxidant have an improved health promoting effect compared to food supplements where marine oil and antioxidants are ingested in separate formulas, e.g. capsules, pills or tablets. The specific formulation of the invention is believed to be of great importance, presenting the essential nutrients and specific health promoting agents (polyunsaturated fatty acids and added antioxidants) to the digestive system and to the cells in a format highly beneficial to the cells and the body.

FIGURES

FIG. 1 shows the effect of marine oils on lipid peroxidation in U937 cells. Cells were incubated for 48 h with different concentrations of omega-3 fatty acids from different vendors as shown in legend. Concentrations are indicated in the X-axis. Y-axis shows the relative levels of lipid peroxidation using DPPP mediated fluorescence as a sensor. Standard deviation is indicated.

EMBODIMENTS

The invention will now be further illustrated with reference to the following non-limiting examples.

Drink According to the Invention

The marine oil used in all preparations was Xalar salmon oil from Marine Harvest Ingredients, batch number: 099000F016. The totox value was below 5 and the preparation were conducted according to functional oil standards.

Example 1

Drink comprising fresh marine omega-3 emulsion and astaxanthin.

|  | % |
|---|---|
| Water, purified | 42.31 |
| Vegetable juice | 45.00 |
| Rosemary Extract 201 | 0.02 |
| Toco 50 | 0.01 |
| Grindsted 3115 | 1.00 |
| Apple juice concentrate | 10.00 |
| Nat lemon aroma | 0.15 |
| Astaxanthin | 0.01 |
| Marine oil | 1.50 |
| sum | 100.00 |

Granini Vegetable juice
Grindsted 3115 from Dansico
Nat lemon aroma from Firmencih
Food grade *Haematococcus pluvialis* powder (esterified astaxanthin complex in the form of *haematococcus pluvialis* algae biomass), supplied by: Sinochem Hebei corporation, 707 Lianmeng, Shijiazhuang, China

Example 2

Drink comprising fresh marine omega-3 emulsion supplied with vitamin C and E.

|  | % | kg |
|---|---|---|
| Rosemary Extract 201 | 0.02 | 0.16 |
| Toco 50 | 0.01 | 0.08 |
| Grindsted 3115 | 1.00 | 8.00 |
| Apple concentrate | 6.05 | 48.40 |
| Pomegranate apple concentrate | 2.40 | 19.20 |
| Aronia concentrate | 0.80 | 6.40 |
| Pear concentrate | 6.49 | 51.92 |
| Water, purified | 81.00 | 648.00 |
| Orange/mandarine Flavour | 0.10 | 0.80 |
| Raspberry Flavour | 0.12 | 0.96 |
| Vitamin C | 0.01 | 0.80 |
| Selenium |  | 0.4 |
| Vitamin E |  | 0.08 |
| Marine oil | 2.00 | 16.00 |
| Sum | 100.00 | 800.80 |

Natural Raspberry Flavour from Firmenich
Natural Orange/Mandarin Flavour from Firmenich
Vitamin E: D-alfa, D-beta, D-delta, D-gamma tocopherol and D-gamma tocotrenol
Vitamin C: Calcium-L-ascorbate (acid neutral)
Selenium: L (+) selenium methionine;
all from G. O. Johnsen

Example 3

Drink comprising emulsified fresh marine omega-3 fatty acids and lycopene and lutein.

|  | % |
|---|---|
| Rosemary extract 201 | 0.020 |
| Toco 50 | 0.01 |
| Grindsted 3115 | 1.00 |
| Whey protein | 0.45 |
| Apple concentrate | 6.23 |
| Pommegranat concentrate | 2.40 |
| Aronia concentrate | 0.88 |
| Pear concentrate | 5.56 |
| Water, purified | 81.48 |
| Orange/mandarine flavour | 0.10 |
| Raspberry flavour | 0.20 |
| Marine oil | 1.50 |
| Lyconat (6% lycopene) | 0.12 |
| Lutenat (10% lutein) | 0.05 |
| sum | 100.00 |

Rosemary exctract 201, Toco 50 and Grindsted 3115 from Dansico
Whey protein from Arla Foods
Natural flavouring agents from Firmenich
Natural lycopene (Lyconat) from Vitatene
Natural lutein (Lutenat) from Vitatene

Example 4

Drink comprising emulsified fresh marine omega-3 fatty acids and lutein.

|  | % |
|---|---|
| Rosemary extract 201 | 0.020 |
| Toco 50 | 0.01 |
| Grindsted 3115 | 1.00 |
| Apple concentrate | 3.23 |
| Pommegranat conc | 1.40 |
| White grape concentrate | 2.56 |
| Soya milk | 58.40 |
| Water, purified | 31.42 |
| Apricot flavour | 0.25 |
| Lemon flavour | 0.10 |
| Marine oil | 1.50 |
| Lutein | 0.11 |
| sum | 100.00 |

Rosemary exctract 201, Toco 50 and Grindsted 3115 from Dansico
Natural flavouring agents from Firmenich
Salmon oil for Marine Harvest Ingredients, Totox below 5 and processed according to functional oil standards
Natural lutein (Lutenat 10% OS) from Vitatene, Italy

Example 5

Drink comprising emulsified fresh marine omega-3 fatty acids and CoQ10 and selenium.

|  | % |
| --- | --- |
| Rosemary extract 201 | 0.02 |
| Toco 50 | 0.01 |
| Whey proteins | 0.35 |
| Grindsted 3115 | 1.20 |
| Apple concentrate | 6.66 |
| Pommegranat concentrate | 1.90 |
| Aronia concentrate | 2.56 |
| Water, purified | 84.15 |
| Mangosteen flavouring | 0.25 |
| Umbu flavouring | 0.10 |
| Marine oil | 2.50 |
| CoQ10 (10%) | 0.30 |
| Selenium | 50 µg |
| Vitamin D | 1.5 µg |
| sum | 100.00 |

Rosemary exctract 201, Toco 50 and Grindsted 3115 from Dansico
Natural flavouring agents from Cargill
Selenium supplied by: Sinochem Hebei corporation, 707 Lianmeng, Shijiazhuang, China
Coenzyme Q10 from DSM
Vitamin D from G. O. Johnsen
Whey proteins (Lacprodan) from Arla Foods

Example 6

Process for Production

1. Oil Phase

The oil is mixed with rosemary extract, Toco 50 (an antioxidant preparation favourable to the stabilization of the oil). It is important that the oil is protected against oxidation during processing. Thereafter, the emulsifier is added (Grindsted 3115) to the oil, mixed gently at room temperature to a homogenous mixture. The flavouring agents are then added.

2. Antioxidants

Oil soluble antioxidants are mixed with the oil phase, and the water soluble antioxidants are mixed with the water phase prior to heating. Optionally, the water soluble antioxidants are mixed with the water phase after heating through specialized systems such as Flexdose (Tetra Pack solution), or added into a sterile tank through an ultra pure process.

3. Water Phase

A tank is filled with purified and deionised water. The oil phase is added to the water phase.

Optionally, the oil phase may be mixed with the water phase after which the emulsifier is added and an emulsion is obtained. The fruit concentrates are then added to the emulsion obtained and mixed thoroughly.

The obtained emulsion may alternatively be subjected to a quick pasteurization (about 90° C. for 8 s), followed by homogenization and cooling to a temperature of 4-8° C.

Finally, the drink is filled on airtight aseptic containers, preferably single dose containers, e.g Tetra Brick about 200 ml and stored at 6-8° C. until use.

Strict oxygen control must be implemented in all steps to avoid oxidation of marine oil.

Health Promoting Effects of the Drink According to the Invention

Materials and Methods

To investigate the physiological effects of the drink according to the invention, oxidation of PUFAs in cell membranes has been analyzed. A fluorescent sensor of lipid peroxidation named diphenyl-1-pyrenylphosphine (DPPP) was used to assess lipid peroxidation. DPPP incorporates rapidly into the cell membrane and upon oxidation emits light, which can be measured by a fluorometer (Okimotoa et al., FEBS Letter, June 2000). Samples according to the invention and samples containing fish oil from commercial available marine oil capsules were analyzed and compared.

Sample Preparation

Drink as described in Example 3 were used and identified as sample 1=Smartfish. The drink contains 900 mg omega-3 pr 200 ml of drink. The amount of lycopene and lutein are 16 mg and 10 mg lutein pr 900 mg omega-3, respectively.

Best before: 15.08.09. Fresh fruity taste and smell. No smell or taste of fish oil could be experienced. Homogenous dark red juicy appearance.

Reference samples were prepared from commercial available capsules containing marine oil.

Reference sample 1=Triomega

Triomega (Lot no: 56416408; Midelfart) containing 620 mg omega-3 pr g oil.

Best before: 06.11.2010. Color: Clear. Odour: Weak but detectable.

Reference sample 2=Omega 3

Omega 3 (Lot no: 58212708, Eldorado) containing 570 mg omega-3 pr g oil.

Best before: 27.10.2010. Color: clear; Odour: weak but detectable

Reference sample 3=Direct Care

CAREMAX (Lot no 71105, Direct Care) containing 600 mg omeg-3 pr g oil.

Best-before: October 2009; Color: brown; Odour: strong

Reference sample 1 and 2 is available in the shops and were bought at the grocery store. Reference sample 3 was ordered via interne.

Marine oils were collected from the capsules with a syringe and mixed with the same emulsifier as used in the drink according to the invention, i.e. Grindsted 3115. 1.5 g of marine oil was mixed with 0.75 g emulsifier (marine oil: emulsifier 2:1). Cell medium was added to give a total volume of 10 ml to yield an oil-in-water emulsion. Addition of medium was followed by vortexing.

Sample 1 is added lycopene and lutein. Thus, the marine oils from capsules were supplemented with lycopene and lutein to correspond to the amount of lycopene and lutein present in sample 1.

Lycopene and lutein were purchased from Sigma-Aldrich and dissolved in DMSO (Sigma-Aldrich) to stock solutions containing 3.6 µg/µl or 2.2 µg/µl, respectively. 10 µl of the stock solutions were added to 316 µl marine oil of the reference samples to achieve corresponding amounts of lycopene and lutein as in sample 1 of the invention. Table 1 below shows the preparation of stock solutions and addition to the reference samples.

TABLE 1

Preparation of stock solutions and addition of lycopene and lutein

|  | Lycopene in DMSO | Lutein in DMSO | Vol added to 3160 µM ω3 |
| --- | --- | --- | --- |
| Stocks | 3.6 µg/µl (1 mg/277 µl DMSO) | 2.2 µg/µl (1 mg/454 µl DMSO) | 10 µl of each |

TABLE 2

Overview of sample preparation

|  | Omega-3 (ω3) | Mol ω3/g | Lycopene | Lutein |
|---|---|---|---|---|
| Sample 1 Smartfish | 900 mg/200 ml juice | 14 μmol/g juice | 16 mg/900 mg ω3 | 10 mg/900 mg ω3 |
| Ref. sample 1 Triomega | 620 mg/g oil | 1.94 mmol/g oil | 11 mg/620 mg ω3 | 6.8 mg/620 mg ω3 |
| Ref. sample 2 Omega 3 | 570 mg/g oil | 1.78 mmol/g oil | 10.1 mg/570 mg ω3 | 10.1 mg/570 mg ω3 |
| Ref sample 3 Direct care | 600 mg/g oil | 1.87 mmol/g oil | 10.7 mg/600 mg ω3 | 10.7 mg/600 mg ω3 |
| For all samples |  |  | 18 μg/mg ω3 | 11 μg/mg ω3 |

Cells

U937 (ATCC No CRL-1593.2™), a human monoblast cell line, which are stably transfected with NF-κB-RE coupled with luciferase. Cells were grown in RPMI+L-glut, 10% FCS, 2× P/S, Hygromycin.

Cells were incubated with sample 1 and reference sample 1-3 in concentrations of omega-3 fatty acids ranging from 1 μM to ~3000 μM for 48 hours. The samples were supplemented with lipoprotein lipase, which hydrolyzes and liberates fatty acids from the glycerol backbone of the triglycerides as described below.

Probe for Lipid Peroxidation:

Dipenyl-1-pyrenylphosphine (DPPP, D7894, lot no 29055W) was purchased from Invitrogen. MW 386.43 g/mol, 5 mg. Excitation/emission: 351/380 nm. Stock solution: 5 mM (5 mg in 2.6 ml DMSO).

Lipase

10 Units of bovine milk lipoprotein lipase (from Sigma-Aldrich, L2254, lot no 114K7430) was added to the cells containing the highest concentrations of omega-3 fatty acids in the marine oils. Following dilution of the samples, the lipase was diluted accordingly. Thus the lowest concentration of the omega-3 rich samples (1 μM) contained 0.003 Units of lipoprotein lipase.

Treatment of Cells and Measurements of DPPP Oxidation, LDH and Protein Content

Sample 1 according to the invention and reference samples 1-3 containing lycopene and lutein were prepared as stock solutions containing 14 000 μM and 300 000 μM of omega-3 fatty acids, respectively. The concentrations of omega-3 fatty acids were calculated on the basis of the omega-3 content listed in the product descriptions. Since the samples are fish oils, the omega-3 fatty acids are presented to cells as triglycerides, and not free fatty acids. They were further diluted to give final concentrations in the cell medium ranging from 1 to 3160 μmol/L in triplicates (see table 5 for plate set up). Lycopene, lutein and lipoprotein lipase were added to dilute samples destined for cells with 3160 μM omega-3, and further diluted according to table 3 and 4. Cells ($10^5$) were seeded in 96 well plates with 100 μl medium. Prior to addition of samples, medium was changed and cells were added 50 μl medium/well. 50 μl of the different dilutions containing all the indicated ingredients were then added to cells. Cells were then incubated for 48 h at 37° C. and prepared for assessment of DPPP fluorescence according to a slightly modified method described by Okimotoa (Okimotoa et al., FEBS Letter, June 2000)

TABLE 3

Dilutions of sample 1 according to the invention

|  | Conc. (μM) Omega-3 | Vol (μL) | Vol Medium (μL) | Total vol (μL) |
|---|---|---|---|---|
| Oil stock | 14000 |  |  | 2000 |
|  | 6320* | 450 | 550 | 1000 |
|  | 2000* | 316 | 684 | 1000 |
|  | 632* | 316 | 684 | 1000 |
|  | 200* | 316 | 684 | 1000 |
|  | 63.2* | 316 | 684 | 1000 |
|  | 20* | 316 | 684 | 1000 |
|  | 6.32* | 316 | 684 | 1000 |
|  | 2* | 316 | 684 | 1000 |

TABLE 4

Dilution of reference samples 1-3

|  | Conc. (μM) Omega-3 | Vol (μL) | Vol Medium (μL) | Total vol (μL) |
|---|---|---|---|---|
| Oil stocks | 300000 |  |  |  |
|  | 6320* | 21 | 979 | 1000 |
|  | 2000* | 316 | 684 | 1000 |
|  | 632* | 316 | 684 | 1000 |
|  | 200* | 316 | 684 | 1000 |
|  | 63.2* | 316 | 684 | 1000 |
|  | 20* | 316 | 684 | 1000 |
|  | 6.32* | 316 | 684 | 1000 |
|  | 2* | 316 | 684 | 1000 |

*Concentrations are indicated as 2× the final conc. in cell medium because it was further diluted when 50 μl of the solutions were added to cells containing 50 μl cell medium.

TABLE 5

Plate setup; Omega-3 concentration

| | DPPP | | | |
|---|---|---|---|---|
| | + | + | + | + |
| | Lipase | | | |
| | + | + | + | + |
| | Sample 1 "Smart-fish" | Ref sample 1 "Triomega" | Ref sample 2 "Omega 3" | Ref sample 3 "Care direct" |
| | 1 2 3 | 4 5 6 | 7 8 9 | 10 11 12 |
| A | 3160 µM | 3160 µM | 3160 µM | 3160 µM |
| B | 1000 µM | 1000 µM | 1000 µM | 1000 µM |
| C | 316 µM | 316 µM | 316 µM | 316 µM |
| D | 100 µM | 100 µM | 100 µM | 100 µM |
| E | 31.6 µM | 31.6 µM | 31.6 µM | 31.6 µM |
| F | 10 µM | 10 µM | 10 µM | 10 µM |
| G | 3.16 µM | 3.16 µM | 3.16 µM | 3.16 µM |
| H | 1 µM | 1 µM | 1 µM | 1 µM |

For DPPP measurements cells were washed 2 times in phosphate buffered saline and added DPPP to a final concentration of 50 µmol/L. This was done in dark conditions to avoid light induced oxidation of DPPP. The cells containing the DPPP were then measured for fluorescence using a spectrofluoremeter (Spectramax Molecular Devices) 3 hours after addition of DPPP.

Protein measurements were done in cells lysates after DPPP assessments. Proteins were measured according to a Bio-rad kit (coloromteric absorbance assay), and used to calculate the relative values.

Results

Table 6 showing normalized fluorescent values in Smart-fish, emulsion (control) and reference samples following incubation of U937 cells for 48 h. Fluorescence is based on oxidation of DPPP with subsequent change in fluorescent intensity. The data are presented as normalized values corrected for protein content in cell lysates. +/−standard deviation is indicated.

TABLE 6

| Omega-3 concentrations | | Sample 1 Smart-fish | Control Emulsion | Ref. sample 1 Triomega | Ref. sample 2 Omega 3 | Ref. sample 3 Care direct |
|---|---|---|---|---|---|---|
| 1 µM | DPPP | 100.0 | 100.0 | 100.0 | 100.0 | 100.0 |
| | SD | ±7.0 | ±7.9 | ±2.1 | ±4.7 | ±9.6 |
| 3.16 µM | DPPP | 98.0 | 100.0 | 97.7 | 101.2 | 101.6 |
| | SD | ±7.5 | ±8.0 | ±1.1 | ±8.6 | ±6.7 |
| 10 µM | DPPP | 97.6 | 98.4 | 106.2 | 106.1 | 111.9 |
| | SD | ±6.2 | ±3.8 | ±5.5 | ±13.3 | ±4.6 |
| 31.6 µM | DPPP | 102.2 | 101.8 | 106.0 | 117.9 | 114.9 |
| | SD | ±9.8 | ±2.1 | ±9.7 | ±17.0 | ±8.9 |
| 100 µM | DPPP | 95.1 | 105.1 | 98.5 | 132.1 | 121.7 |
| | SD | ±9.9 | ±3.7 | ±0.8 | ±23.5 | ±11.8 |
| 316 µM | DPPP | 94.2 | 113.3 | 107.2 | 132.9 | 137.1 |
| | SD | ±14.2 | ±3.7 | ±11.1 | ±19.2 | ±8.1 |
| 1000 µM | DPPP | 97.2 | 102.3 | 110.6 | 136.3 | 168.9 |
| | SD | ±7.6 | ±11.5 | ±2.7 | ±43.6 | ±11.7 |
| 3160 µM | DPPP | 95.2 | 98.2 | 121.9 | 176.0 | 239.1 |
| | SD | ±15.1 | ±9.2 | ±13.0 | ±31.7 | ±12.8 |

Effect of Marine Oils on Lipid Peroxidation in U937 Cells

The results show that no detectable lipid peroxidation was observed in cells incubated with the sample according to the invention at any of the doses used, when compared with controls receiving cell medium alone (data not shown) or an emulsion with no oil added. For the reference samples, a dose dependent increase in lipid peroxidation was found. Notably, the degree of lipid peroxidation was coinciding with the odour and color appearance of the marine oil products. Odour and color is indicative of oxidation of the oil. Addition of lycopene and lutein to the oils in comparable concentrations as in sample 1 according to the invention was not sufficient to inhibit lipid peroxidation.

As seen in the table 6 and in FIG. 1, no effect in DPPP mediated fluorescence was observed with the two lowest concentrations, i.e. 1 µM and 3.16 µM, of the sample according to the invention or the reference samples. This indicates that at these concentrations no detectable lipid peroxidation in the cell membrane has occurred. At higher concentrations, a weak increase is observed for all the oils, except the sample according to the invention. From 10 µM and upwards, a gradual change in signal seems to be evident. At 100 µM there is a significant difference between sample 1 according to the invention and reference sample 3, (Care direct) (p=0.045), while a tendency is noticed for reference sample 1 (Triomega) and reference sample 2 (Omega 3). At 316 µM and 1000 µM a significant difference between the sample according to the invention and all reference samples were found. The difference was even more pronounced at the highest concentration i.e. 3160 µM The highest degree of lipid peroxidation was found with reference sample 3 (Care direct), while reference sample 1 (Triomega) gave the lowest degree of lipid peroxidation of the three commercially available marine oil products. Notably, the sample according to the invention did not affect lipid peroxidation at any of the concentrations used.

Studies in humans have shown that ingestion of omega-3 fatty acids as supplements can reach 10-20% of total fatty acids in plasma (review by Masson et al., J. Cardiovasc. Med, 2007). Since the plasma concentrations of total fatty acids as triglycerides are in the range of 1-5 mM, fish oil plasma concentrations can reach 100 to 1000 µM following oral intake of fish oil. In the present study, we found increased lipid peroxidation by all the reference samples in this concentration range, which can be regarded as physiologically relevant.

Surprisingly we have found that Sample 1 according to the invention offer a greater protection against lipid peroxidation than the reference samples. No detectable change in lipid peroxidation was found for any of the concentrations used for sample 1. A dose-dependent increase in lipid peroxidation were observed for all tree reference samples, despite the fact that the shelf life of all capsules was not expired and all capsules contained antioxidants to stabilize the fish oil during storage. The effect on lipid peroxidation of capsule based marine oils differed between the suppliers. The strongest odour of fish oil and colouring of oil (brown), which are indicative of oxidation was found in reference sample 3 (Care direct), which also resulted in more lipid peroxidation. The shelf life of this product expires October 2009. Reference sample 1 and 2 expiring October/November 2010 did also induce significant lipid peroxidation of the cells. The addition of lycopene and lutein to the reference samples was evidently not affording enough protection to inhibit lipid peroxidation.

Thus, the present invention provides a new drink formula wherein the fresh fish oil and the added antioxidants are protecting the cells against oxidative stress in a much more efficient way than commercially available fish oils added corresponding amounts of antioxidants. As oxidative stress is believed to be responsible for a long series of diseases, this new drink formula has a great potential as a health promoting drink.

The invention claimed is:

1. A drink comprising fresh marine oil in an oil-in-water emulsion wherein the marine oil has a totox value below 10, and further comprising at least one added antioxidant not naturally present in said oil-in-water emulsion, wherein the content of marine oil is about 0.5% to 5% by weight based on the total weight of the drink and the at least one added antioxidant is a combination of added lutein and added lycopene that are not naturally present in the water or oil phase, but are added separately to the drink.

2. The drink according to claim 1, wherein the totox value is below 8.

3. The drink according to claim 2, wherein the totox value is below 5.

4. The drink according to claim 1, wherein the added lutein is present in an amount of 0.005% to 0.11% by weight based on total weight of the drink.

5. The drink according to claim 4, wherein the content of marine oil is about 0.5% to 3% by weight based on the total weight of the drink.

6. The drink according to claim 5, wherein the content of marine oil is about 1.5% to 2.5% by weight based on the total weight of the drink.

7. The drink according to claim 1, wherein the water phase in the oil-in-water emulsion comprises natural antioxidants naturally present in the water phase.

8. The drink according to claim 7, wherein the water phase is a juice base.

9. The drink according to claim 7, wherein the water phase is a tea base.

10. The drink according to claim 1, wherein the water phase further comprises protein.

11. The drink according to claim 10, wherein the protein is whey protein.

12. The drink according to claim 1, further comprising polyunsaturated vegetable oil.

\* \* \* \* \*